United States Patent [19]

Forman

[11] 4,114,640
[45] Sep. 19, 1978

[54] DRAIN VALVE

[75] Inventor: Hugh M. Forman, Waukesha, Wis.

[73] Assignee: Will Ross Inc., Milwaukee, Wis.

[21] Appl. No.: 758,114

[22] Filed: Jan. 10, 1977

[51] Int. Cl.² ............................................. F16K 7/06
[52] U.S. Cl. ..................................... 137/381; 251/9; 251/75
[58] Field of Search ...................... 251/4, 6, 7, 9, 10, 251/340; 222/529, 498; 137/381

[56] References Cited

U.S. PATENT DOCUMENTS

| | | | |
|---|---|---|---|
| 2,475,164 | 7/1949 | Thomsen | 137/381 |
| 2,969,064 | 1/1961 | Metz | 251/9 X |
| 3,610,566 | 10/1971 | Rychlik | 251/9 |
| 3,779,507 | 12/1973 | Clarke | 251/9 |

FOREIGN PATENT DOCUMENTS 646,167  11/1950  United Kingdom ..................... 251/9

Primary Examiner—Martin P. Schwadron
Assistant Examiner—Richard Gerard
Attorney, Agent, or Firm—John A. Dhuey

[57] ABSTRACT

A valve assembly is described for closure of resilient tubes and protection of the ends of such tubing from contamination when the valve is in its closed position. The valve assembly is fabricated from two trough-like members which are connected by a linkage having bi-stable characteristics to facilitate one-handed operation. The assembly is particularly useful when employed at the end of drainage bag outlet tubes in hospital applications, where the likelihood of contamination of the tube end must be minimized.

12 Claims, 7 Drawing Figures

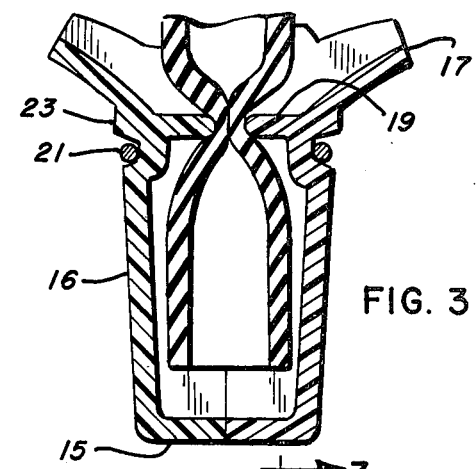
FIG. 3
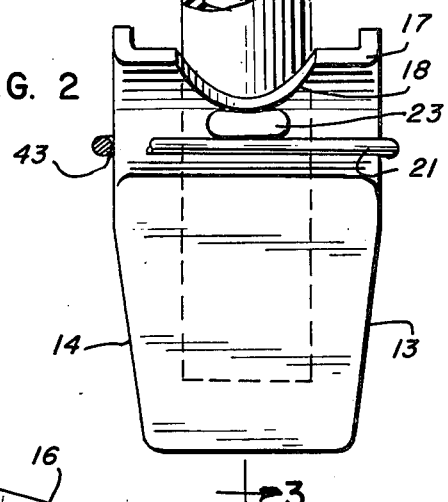
FIG. 2
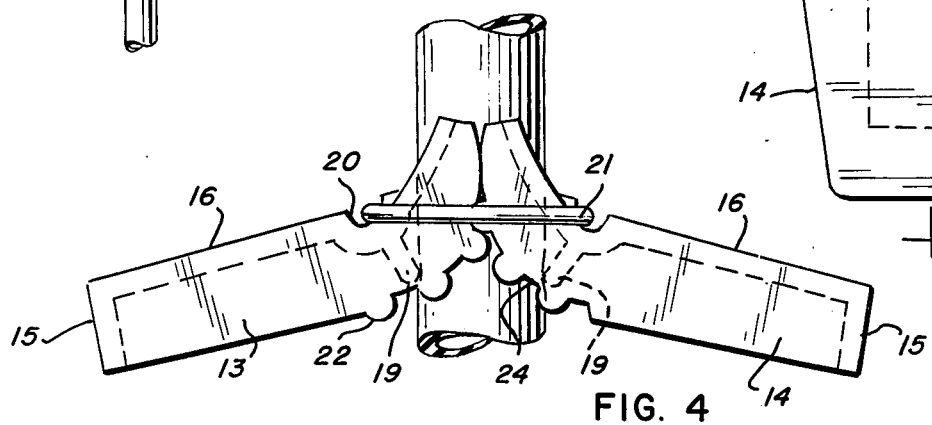
FIG. 4
FIG. 5 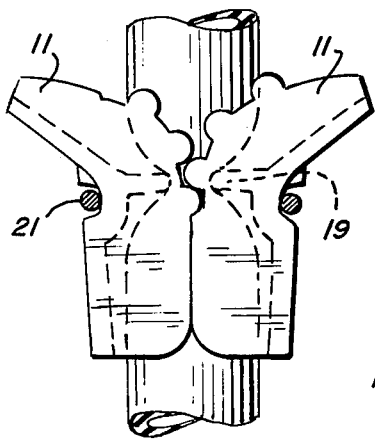  FIG. 6 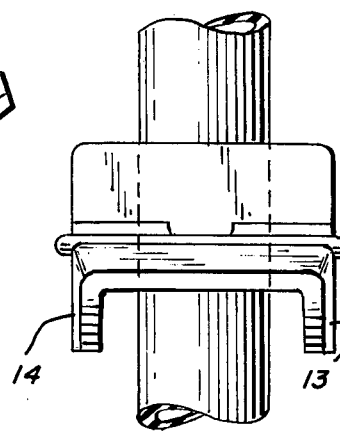  FIG. 7 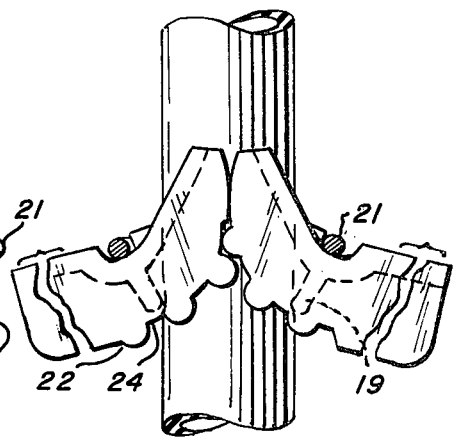

DRAIN VALVE

Conventional fluid collection containers in hospital applications generally have an outlet tube to facilitate emptying of the container and obtaining fluid samples for laboratory analysis. The outlet tubes have heretofore been closed by means of a simple clamp on the tube intermediate the container and the tube outlet. The tube outlet generally remains exposed to the hospital room environment.

It is well known that bacterial growth can occur within a drainage bag and subsequently infect a patient who is connected to the collection container. Thus, it is important to provide every precaution against contamination of fluid within the bag and contamination of associated tubing which may permit bacteria to enter the bag. It is apparent that the exposed end of the drainage bag outlet tubing is a prime source of possible bacterial entrance into the drainage container.

Simply covering the exposed tubing end by a cap or other means is not entirely satisfactory since the cap must be placed somewhere while the drainage bag is emptied. The cap may be contaminated at its storage location and upon replacement may in fact magnify the problem it was intended to solve by carrying the bacteria to the tubing end. Furthermore, the combined operation of cap removal, valve clamp actuation to empty the bag, and reattachment of the cap is inefficient and cumbersome.

In order to correct the above-noted deficiencies of prior systems, there is described herein a valve assembly which closes the outlet tubing and encloses the end of the tube in one operation. Also, the valve assembly may be operated by one hand which greatly facilitates the overall fluid collection operation.

The pivotal arrangement of the valve assembly provides for bistable operation. The spring action supplied by the outlet tubing holds the valve closed or moves it to the full open position.

The invention will be described with reference to the following drawings in which:

FIG. 2 is a front view of one embodiment of the valve clamp positioned on the tube in its closed configuration;

FIG. 3 is a cross-sectional view of the valveclamp of FIG. 2 along line 3—3;

FIG. 4 is a side view of the valve-clamp shown in its open configuration;

FIG. 5 is a side view of another embodiment of the valve-clamp in its closed position;

FIG. 6 is a front view of the valve-clamp of FIG. 5 in its open position; and

FIG. 7 is a side view of the valve-clamp of FIG. 5 in its open configuration.

Figure 1:
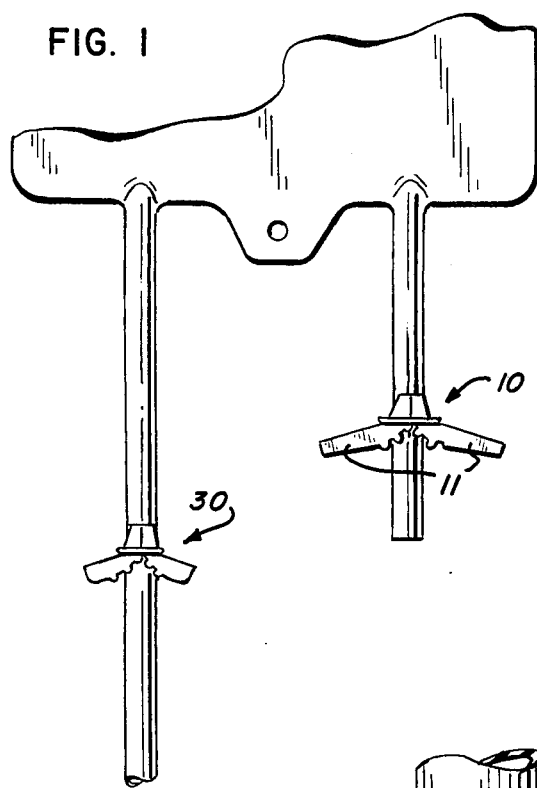
FIG. 1 is a perspective view of the valve clamp positioned on the tubing in an open configuration.

In a preferred embodiment of the invention, valve-clamp assembly 10 is formed from similar members 11 connected in an opposed configuration by an over-center arrangement. Each member 11 is trough-like and is formed with side walls 13 and 14 and closure wall 15 at its bottom end, and outer wall 16. The top end of member 11 is substantially open. In a preferred embodiment side walls 13 and 14 extend outwardly at the top end of member 11 and converge with outer wall 16 which also is curved outwardly at its top end to form a top end wall 17. Top, end wall 17 is formed with a recessed portion 18 through which the drainage bag outlet tubing can pass when the valve-clamp assembly 10 is in its open configuration. An upstanding projection 19 is formed near the upper end of member 11 on the inside of the trough formed by walls 13, 14 and 16. Projection 19 is integrally formed with member 11 and usually extends the width of the trough and is of lesser height than the width of side walls 13 and 14.

Hinging means are provided by grooves 20 and retention ring 21. Groove 20 is formed in walls 13, 14 and 16 and is adapted to retain a portion of retention ring 21 which encompasses the opposed members 11. Retention ring 21 may be continuous or discontinuous. Retention ring 21 is formed from rigid, semi-rigid or elastic materials which provide for a certain amount of yielding during valve operation. Alternate hinging means can be provided between members 11. However, the above-described arrangement is low-cost and easily employed with molded parts.

Hinging means such as groove 20 and retention means 21 sometimes are not adequate to keep members 11 aligned during the opening and closing operations. It is therefore desirable to provide additional alignment means between the opposing members 11 so that they do not become skewed, particularly when the valve assembly is being operated. For example, there are provided a plurality of projections 22 on the upper curved portions of walls 13 of members 11. Projections 22 are arranged so that they can co-act with their opposing counterparts when opposing members 11 rotate about the hinging mechanism. Projections 22 are angularly positioned with respect to side wall 13 and pivot 20, one half tooth spacing rotated compared to projections on side wall 14. Accordingly, when members 11 are opposed, projections on each member co-act with spaces 24 on the opposing member. Projections 22 can be gear teeth or similarly designed coacting members which are able to mesh during rotational operation without appreciable free play.

The flared top portions of members 11, ending in top end walls 17, provide a convenient grip on the valve-clamp assembly for actuation of the valve. By simply using a thumb and forefinger, a hospital aid can push inwardly on walls 17. The inward force created about the off-center hinging means causes opposed members 11 to swing outwardly at their lower ends. Projections 19 are thereby removed from their impingement position on the resilient tube, which effects opening of the internal tubular bore and permits fluid flow through the outlet. When the necessary flow operation has been completed, the aide, again using only one hand, can press inwardly on back walls 16 at a point below the hinged connection to cause members 11 to snap together to their closed configuration. A bistable operation is afforded wherein the tube biases the members 11 to a closed position when the retaining ring 21 is positioned below the projections (FIG. 5) and biases the members to an open position when the ring is positioned above the projections (FIG. 4). If walls 17 are curved up more sharply from the pivot point, groove 18 can be eliminated and walls 17 present an uninterrupted surface.

Valve-clamp assembly 10 is positioned on the drainage bag tubing outlet so that the end of the outlet tube is enclosed in the channel formed by opposed members 11 when in their closed configuration. The end of the tube then is protected from the hospital room environment whenever the valve is closed.

An alternate embodiment of the invention is described in FIGS. 5—7 for use in situations where it is not necessary to protect the end of the drainage tubing. Valve 30 is similar in all respects to valve 10 described previously except for the absence in valve 30 of end walls 15 on the two opposed members 11. Accordingly, the valve consists of identical opposed members 11 having side walls 13 and 14 and outer wall 16. A retaining ring 21 encompasses members 11 and is retained in groove 20. Projections 19 extend upwardly from the troughlike space formed on the inside of each member 11 and are adapted to inpinge upon the drainage tube in the closed configuration to prevent fluid flow therethrough. Alignment means 22 are provided on side walls 13 and 14 of opposed members 11 in the same manner as described for valve 10 above. Operation of valve 30 is substantially the same as that of valve 10, except that valve 30 does not cover the end of the drainage tube.

The valve-clamps of this invention are most conveniently manufactured by conventional plastic molding operations. Satisfactory materials are polyproplene and the like.

Rings 21 preferably are inwardly bowed on the sides which ride in grooves 20, to accommodate tolerances. Also the rings may have inwardly bowed sides or projections 43 engaging walls 13 and 14 to provide a braking action during the movement from open to closed. Such a feature also provides intermediate positioning if the braking force exceeds the force exerted on projections 19 by the resilient tube. Additionally, to retain the ring in the groove during assembly a ridge or projection 23 can be provided on outer wall 16.

In another alternate embodiment, opposed members 11 can be of semicircular cross-section to form an arcuately shaped trough. A lower end wall 15 is provided in those cases where the valve is intended to cover the drainage tube end. The remaining aspects of the valve remain substantially unchanged except to conform to the shape of the semicircular troughs.

Although the invention has been described, in its preferred embodiments, with respect to the drawings, they are intended for illustration purposes and not meant to unduly limit the invention. Various modifications will be apparent to those skilled in the art without departing from the spirit and scope of the invention. Materials of manufacture are not critical. Members 11 are conveniently molded according to usual methods from appropriate polymeric materials.

What is claimed is:

1. A valve assembly for use on the end of a resilient tube to control fluid flow within the tube comprising:
   a pair of opposed, trough-like members, each member closed at a first end thereof and substantially open at a second end thereof and having an upstanding projection intermediate said first and second ends, said members being adapted to receive the end of said resilient tube therebetween and said projections being adapted to engage the wall of said resilient tube and collapse said tube, said members being movable from a closed position preventing flow through said tube to an open position permitting flow through said tube, said closed ends of said members coacting to enclose the end of said tube when said members are in said closed position; and
   means for hingedly connecting said members in an opposed relationship, said hinging means being movable from a first position below said projections when said members are in said closed position preventing flow of fluid through said tube to a second position above said projections when said members are in said open position permitting flow of fluid through said tube, whereby the force on said projections by said tube biases said members to said closed position when said hinging means is at said first position and biases said members to said open position when said hinging means is at said second position to provide bistable operation of said valve assembly.

2. A valve assembly as in claim 1, wherein said upstanding projections in said opposing members are directly opposed to each other when said assembly is in its closed position.

3. A valve assembly as in claim 1, further comprising rotational alignment means associated with said members to retain said members in an aligned, opposed position during valve operation.

4. A valve assembly as in claim 3, wherein said rotational alignment means comprises a set of co-acting projections on opposing sides of said members adjacent to said second ends thereof.

5. A valve assembly as in claim 3, wherein said upstanding projections in said members are directly opposed to each other when said assembly is in its closed position.

6. A valve assembly as in claim 1, wherein said second ends of said members extend outwardly.

7. A valve assembly as in claim 1 wherein said members are substantially rectangular channels.

8. A valve assembly for use on the end of a resilient tube to control fluid flow within the tube comprising:
   a pair of opposed, substantially semi-circular, trough-like members, each member closed at a first, bottom end thereof and substantially open at a second, top end thereof and having an integral, upstanding projection intermediate said first and second ends and extending across said member, said members being adapted to receive the end of said resilient tube therebetween and said projections being adapted to engage the wall of said resilient tube and collapse said tube, said members being movable from a closed position preventing flow through said tube to an open positon permitting flow through said tube, said closed ends of said members coacting to enclose the end of said tube when said members are in said closed position;
   means for hingedly connecting said members in an opposed relationship, said hinging means being movable from a first position below said projections when said members are in said closed position preventing flow of fluid through said tube to a second position above said projections when said members are in said open position permitting flow of fluid through said tube; and
   rotational alignment means associated with said members to retain them in a generally opposed relationship, whereby the force on said projections by said tube biases said members to said closed position when said hinging means is at said first position and biases said members to said open position when said hinging means is at said second position to provide bi-stable operation of said valve assembly.

9. A valve assembly as in claim 8 wherein said rotational alignment means comprises a set of co-acting projections on each side of said members adjacent the top end thereof, the alignment of said projections differing from one side to the other by one half tooth spacing.

10. A valve assembly as in claim 9 wherein said hinging means comprises a groove in the outer wall of each of said members and a retention ring in said groove encompassing said members.

11. A valve assembly as in claim 10, wherein said top ends of said first and second members extend outwardly to provide gripping means on said assembly.

12. A valve assembly for control of fluid flow in a resilient tube comprising:

a pair of opposed, trough-like members, each member open at both ends thereof and having an upstanding projection intermediate said ends, said members being adapted to receive a portion of said resilient tube therebetween and said projections being adapted to engage the wall of said resilient tube and collapse said tube, said members being movable from a closed position preventing flow through said tube to an open position permitting flow through said tube; and means for hingedly connecting said members in an opposed relationship, said hinging means being movable from a first position below said projections when said members are in said closed position preventing flow of fluid through said tube to a second position above said projections when said members are in said open position permitting flow of fluid through said tube, whereby the force on said projections by said tube biases said members to said closed position when said hinging means is at said first position and biases said members to said open position when said hinging means is at said second position to provide bistable operation of said valve assembly.

* * * * *